Figure 1:
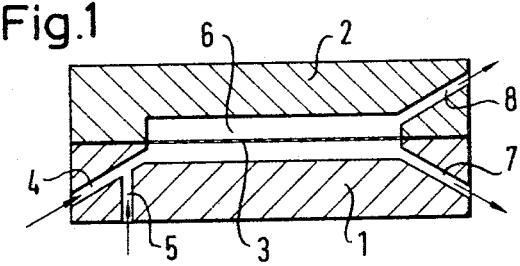

United States Patent [19]

Goldie et al.

[11] 4,251,360
[45] Feb. 17, 1981

[54] METHOD AND APPARATUS FOR THE DETECTION OF A SPECIFIC BINDING PROTEIN

[76] Inventors: David J. Goldie, 1 Radnor Rd.; Adel Abbas A. Ismail, 43 Old Sneed Rd.; Peter M. West, 6 York Gardens, all of Bristol, England

[21] Appl. No.: 53,887

[22] Filed: Jul. 2, 1979

Related U.S. Application Data

[63] Continuation of Ser. No. 833,617, Sep. 15, 1977, abandoned.

[30] Foreign Application Priority Data

Sep. 18, 1976 [GB] United Kingdom ............... 39018/76
Aug. 12, 1977 [DE] Fed. Rep. of Germany ....... 2736527

[51] Int. Cl.$^3$ ............................................. B01D 13/00
[52] U.S. Cl. ............................ 424/1.5; 210/650; 230.3 23/230.6; 435/7; 435/8; 424/12
[58] Field of Search ................. 210/21, 22, 23, 321 R, 210/321 A, 321 B, 42 A; 23/230.6, 230 R; 55/158

[56] References Cited

U.S. PATENT DOCUMENTS

| | | | |
|---|---|---|---|
| 3,203,865 | 8/1965 | Koehler et al. | 210/22 X |
| 3,268,441 | 8/1966 | Lindstrom | 210/22 |
| 3,901,654 | 8/1975 | Gross | 23/230 R |
| 3,919,075 | 11/1975 | Parc et al. | 210/96.2 |
| 4,088,746 | 5/1978 | Blakemore et al. | 23/230.6 |
| 4,089,778 | 5/1978 | Gauger | 210/23 F |

Primary Examiner—John Adee
Attorney, Agent, or Firm—Sprung, Felfe, Horn, Lynch & Kramer

[57] ABSTRACT

The invention provides a method for detecting and determining one component of the reaction between a specific binding protein, e.g., an antibody, and the corresponding bindable substance, e.g., an antigen, by utilizing the affinity of these components for binding one another, in an automated system utilizing a continuously flowing stream of liquid. The method is carried out by introducing successive mixtures of the sample specimen with a set amount of one component of the reaction in tagged form and another, carrier-bound, component, into the liquid stream so that the individual mixtures remain separate, incubating the mixtures and continuously introducing same into a separating system in which at least a portion of the liquid phase is separated from the solid phase, and measuring the amount of the tagged component in one of the separated phases as a measure of the unknown component to be detected. For instance, an unknown antigen in a serum sample is contacted with a solid carrier bound antibody, the mixture incubated, the antigen now bound to the solid phase antibody, removed from the other mixture components and reacted with an additional marked antibody acting against the antigen, to form a sandwich containing solid-bound antibody/antigen/marked antibody, and then separating the solid phase from the liquid phase containing the remaining free-tagged antibody and determining the tagged antibody in either fraction as a measure of the serum antigen initially present.

12 Claims, 5 Drawing Figures

T4 ENZYME IMMUNE TEST
ESTABLISHMENT OF A STANDARD CURVE
$mE_{RECORDING} = mE_{STANDARD} - mE_{C_0}$

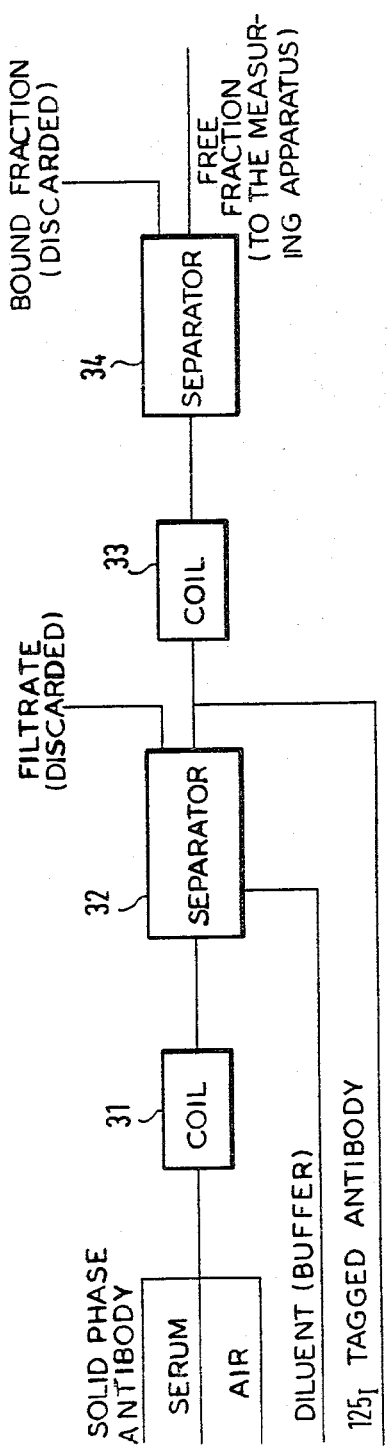

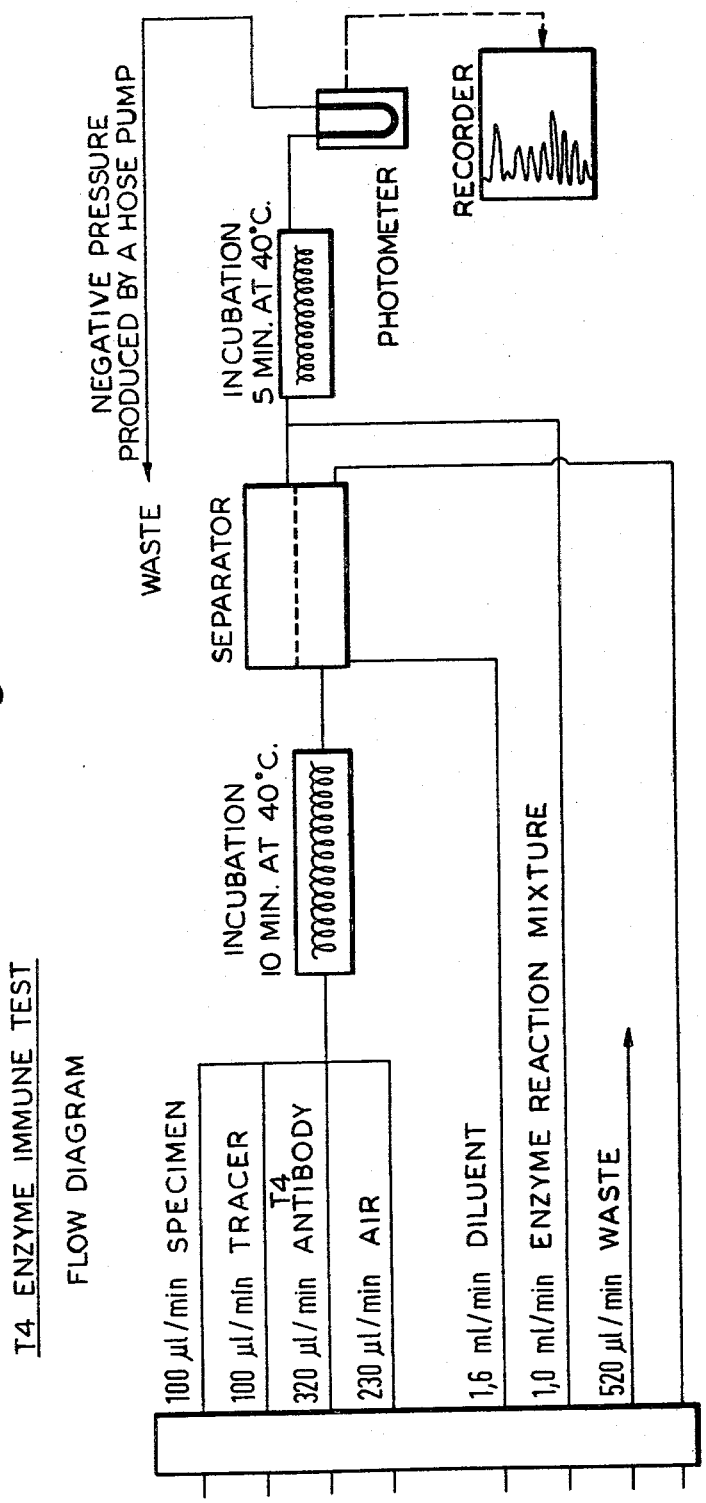

METHOD AND APPARATUS FOR THE DETECTION OF A SPECIFIC BINDING PROTEIN

This is a continuation of application Ser. No. 833,617, filed Sept. 15, 1977, now abandoned.

The invention relates to a method for the detection and determination of one component of the reaction between a specific binding protein and the corresponding bindable substance by using the affinity which these components have for binding one another in an automated system having a continuously flowing stream of liquid, especially an immune test method.

The immune test methods (i.e., the radio-immuno assay (RIA), the enzyme immuno assay (EIA) and the fluorescent immuno assay (FIA) are used world-wide in clinical laboratories. Although originally used in the field of endocrinology, these techniques are sometimes applied to many different fields, including immunology, oncology, clinical pharmacology, microbiology and hematology. Since antibodies can be produced which have a strong affinity for both immunogenic and nonimmunogenic substances, it is possible to accomplish determinations of virtually any compound in very low concentration. Furthermore, the determination can be performed in a relatively impure specimen which is only slightly or not at all purified prior to the analysis.

The precision of such immune tests as the radio-immune test and similar methods of analysis has thus far been relatively low in comparison to other methods being practiced in clinical chemistry laboratories. This is probably because most immune tests are presently performed manually, resulting in problems such as relatively low precision, low throughput, personnel fatigue, and the tediousness of the method. Automation has long been desired in this field; the systems which are commercially available at the present time, such as the LKB, Baird and Tatlock, Micromedic and Centria systems, are discrete analysis systems comprising the use of sample diluters in which a series of samples is delivered to the sample diluter. Furthermore, in some of the steps manual intervention is necessary, such as the removal of the sample rack from the incubator, the centrifugation, the separation of the supernatant fluids, and the transfer to a counting device. In general, these systems are expensive, mechanically unreliable, of relatively poor flexibility, and they generally offer only slight advantages.

Therefore, an effort has been made to create a relatively simple, flexible and fully automatic method that will be suitable for all laboratories. The attractiveness of this method would be that one would be able to avail oneself of the apparatus and skills currently available in a somewhat modern laboratory for clinical chemistry. The method should be flexible and versatile, so that all commonly practiced analyses can be performed with minimum difficulty. Lastly, the process must be inexpensive to perform, and in comparison to the conventional, manually performed, semi-automatic or automatic radio-immune tests and other such tests, it should involve no great operating cost.

A completely automated process using a continuously flowing stream of liquid would certainly fulfill the requirements set forth above. The most critical parts of such a process are, on the one hand, the apparatus which separates the free radicals from the tagged radicals present in the insoluble phase, and, on the other hand, in the case of the radio-immune tests, but not in the others, a counter for the determination of the radioactivity. In Anal. Biochem 65 (1975) 355–361, an automatic continuous-flow system is described which uses antibodies bound to red blood corpuscles. To separate the tagged antigen bound to the antibody from the free radical, the erythrocytes are flocculated or agglutinated with polybrene (hexamethrine bromide) and separated from the supernatant liquid by decantation. In Clin. Chim. Acta, 63 (1975) 69, a solid-phase system is described, which is based on the use of antibodies which are covalently bound to iron oxide coated with polymer (Enzacryl). Both for the mixing of the reactants and for the separation of the tracer bonded to the antibody from the free fraction an electromagnet is used. This principle is the basis for a completely automated system.

Recently there has been reported an automatic on-line system by the name of "Gammaflow", in which the separation of the free ligand from the bound, tagged ligands is accomplished by means of a mixed-bed separating column of active carbon and Dowex resin.

All of the known, fully automatic, continuous-flow systems, however, have a number of disadvantages or limitations. The system using antibodies bound to red blood corpuscles is not suitable for a low throughput (10 specimens per hour) and is of low sensitivity and low precision. The system comprising the use of magnetic particles requires an extremely expensive magnetic separation, which makes the apparatus complicated and expensive. The use of a mixed-bed column for the separation of the bound from the free radicals also has its limitations, since the system cannot be used universally for effectively separating all types of antigenic material. For example, such a column cannot be used to separate immunoglobulins as well as antigens of high molecular weight. The system is also unsuitable for the enzyme immune test in which the charge and mass difference between the bound radicals and the free radicals is very slight.

The present invention is therefore addressed to the problem of creating a simple, flexible and fully automatic process which is suitable especially for the performance of the radio-immune test, the enzyme immune test and the fluorescent immune test.

The present invention method is capable of detecting and determining one component of the reaction between a specific binding protein and the corresponding bindable substance by utilizing the affinity of these components for binding one another, in an automated system with a continuously flowing stream of liquid. The method is carried out by introducing successive mixtures of the sample specimen with a set amount of one component of the reaction in tagged form and another, carrier-bound component into the liquid stream so that the individual mixtures remain separate, incubating the mixtures and continuously introducing same into a separating system which, after the carrier has been insolubilized if necessary, at least a portion of the liquid phase is separated from the solid phase, and measuring the amount of the tagged component in one of the separated phases as a measure of the unknown component to be detected.

In the case of the radio-immune test, the measurement is performed with a counter wherein the radioactivity of successive amounts of the phase to be measured is determined. In the case of the fluorescent immune test and of the enzyme immune test, a fluorimeter and a colorimeter are used for the detection and for the determination.

As specific binding protein, antibodies, anti-antibodies, hormone receptors, other proteins capable of binding hormones, such as for example the thyroxin-binding globulin TBG, intrinsic factor, and the like, come within the scope of the invention.

The corresponding bindable substance is understood as a compound which is capable of entering into a generally complex-like bond with the specific binding protein. Typical examples are antigens, haptenes, steroids, antibodies and other substances capable of forming a bond with a specific binding protein.

At least one of the components of the bindable substances, that is, the specific binding protein or the substance that can be bound thereby, is used in marked form. It can be either the specific binding protein or the corresponding bindable substance. The tagging method can be, for example, the introduction of radioactive atoms or groups, enzyme, coenzyme or substrate tagging, or the introduction of fluorescent or light-absorbing substances. Other methods of tagging can be used, in which the radical is excited by some other physical method, such as electron-spin resonance, for example.

Typical examples of radioactive atoms which can be used within the scope of the invention are iodine, tritium, sulfur, selenium, chromium, carbon and phosphorus. Enzymes frequently used for tagging are, for example, peroxidase, glucose oxidase, alkaline phosphatase and $\beta$-glucosidase. Typical suitable fluorescent substituents are rhodamine, fluorescein isothiocyanate (FITC) and umbelliferyl derivatives.

The tagged component of the reaction (the tracer) can be the same substance as the one to be determined in the process—for instance a tagged antigen where the determination of an antigen is involved. The tracer, however, can also be an additional substance capable of forming a bond with the component that is to be determined—for example, another tagged antibody.

The carrier can be an insoluble, particulate or cellular material, such as porous sephadex, porous sepharose, microcrystalline cellulose, latex, glass spheres, or cells such as erythrocytes, to which the antibody or antigen is covalently bonded. The bulkiness or volume of this carrier does not interfere with the antigen-antibody reaction and permits an adequate separation of the bound radicals from the free radicals. Alternatively, porous particulate carrier materials capable of ion exchange (such as an ion exchange gel, sephadex, or a resin) can be used for the purpose of separating the unbound, tagged component, such as the antigen for example, from the portion of the tagged component that forms a bond with the other specific bond component, such as the antibody, for example. This embodiment of the invention is suitable for components which behave like anionic or cationic radicals, such as many of the haptenes for example. In this embodiment, the antibodies, for example, are not linked to a particulate carrier but are used as they are, after a suitable dilution of the antiserum.

As a rule, an already solid, particulate carrier is used in the method of the invention. It is also possible, however, to use a liquid, but precipitatable carrier, preferably a reversibly precipitatable carrier. Such carriers are carriers which are not always in solid form. An example would be a latex-on-polyacrylamide base which is liquid or solid depending on the pH value. This embodiment of the invention has the advantage that the actual immune reaction can be performed in a homogeneous liquid phase, but prior to the separation of the phases the carrier is transformed to the solid form, for example by changing the pH value. In the preferred embodiment, the precipitated carrier can then be reversibly re-liquefied, which has advantages for the accuracy of the measurement reaction if the phase that is subjected to the measurement is the one in which the solid particles are contained.

The precipitation of the carrier can be accomplished to special advantage by the current of diluent which, in the preferred embodiment of the invention, is fed in just before the filter membrane is reached, and after the dilution-forced filtration which will be explained further below. The diluent can thus consist, for example, of an organic liquid, a salt solution, or a buffer solution, which produces the precipitation by changing the ion concentration, the pH value, or the like.

The separation of the bound and tagged component from the free tagged component is preferably achieved by using a high-porosity membrane. The liquid stream is made to flow past one side of the membrane after being diluted upstream in order to increase the pressure. A negative pressure can also be applied to the other side (filtrate side) of the membrane. The first phase is therefore obtained on the filtrate side, while the second phase, containing the insolubles, is obtained downstream from the retentate side. The amount and the nature of the diluent and/or the amount of the liquid filtered through the membrane can be as desired. This technique is referred to as filtration forced by dilution, or dilution-forced filtration.

Although a number of problems might be expected in applying a continuous-flow system to the immune test, they have surprisingly not been encountered to any appreciable extent. These problems include the difficulty of separating the bound and the tagged marked component at the end of the determination, an insufficient incubation time preventing the reaction from going so far as to result in a satisfactory precision and sensitivity, the difficulty of pumping small amounts of tagged component since there is especially a tendency for adsorption losses to occur in the tubing of the system, and intermingling problems. Preliminary studies, however, have shown that small amounts of tagged and untagged component can be pumped in a continuous-flow system, by the use of air segments for example, without encountering serious problems with regard to adsorption losses or intermingling of the materials.

Figure 2:
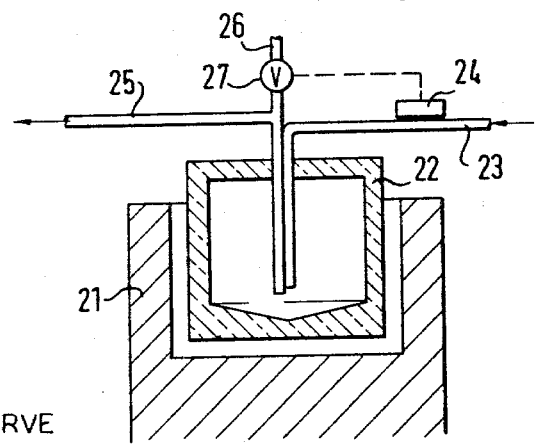
Figure 5:
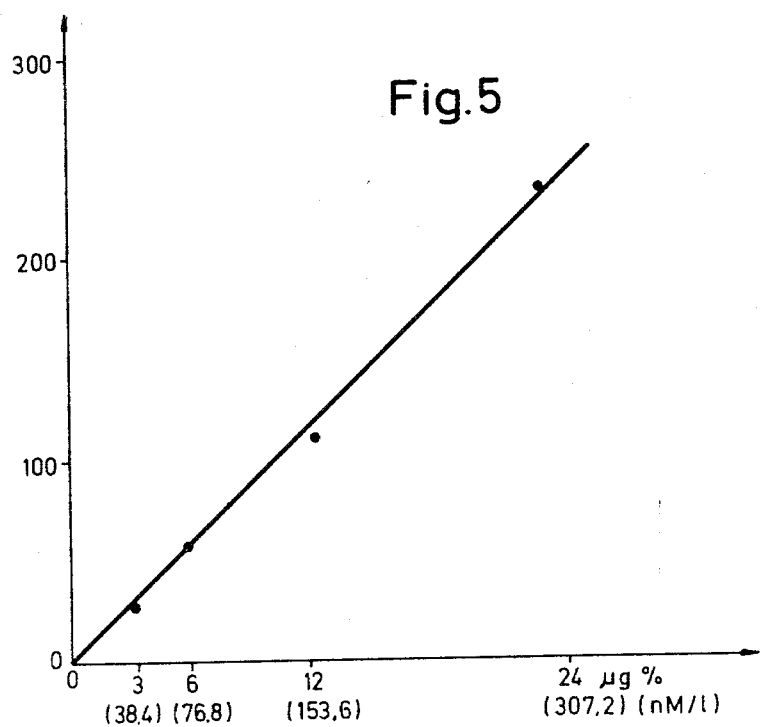

To further explain the invention, reference is had to a number of embodiments illustrated in the drawing hereof, wherein:

FIG. 1 is a diagrammatic cross-sectional view of a separating device of the invention, FIG. 2 is a diagrammatic vertical cross section taken through a radioactivity counting head, FIG. 3 is a block diagram of a radio-immune test system of the invention, FIG. 4 is a block diagram of an enzyme immune test system of the invention, and FIG. 5 is a standard curve established with the system represented in FIG. 4.

The method utilizes in the initial steps conventional continuous flow systems and apparatus, which do not require detailed explanation. The samples of the tracers, i.e., the tagged antigen and the component present in the solid phase, such as the antibody for example, are fed in precisely metered amounts determined by the size of the tube of the tubular distributor. Between the samples is a wash liquid which can be identified characteristically, by staining, for example. This is important only in the case of the radio-immune test, but not in other immune test systems, because the counting device can be controlled such that it will select the amount to be determined on the basis of this characteristic property. The steam, broken up into segments by intervening air segments, is pumped through a controlled-temperature coil of tubing, whereby a thorough mixing of the reagents is accomplished during the incubation time. The incubation time can amount to 25 minutes or less. The liquid stream is then transferred to the separating apparatus, which is represented in FIG. 1. In the latter a dilution-forced filtration is performed. It comprises a divided block consisting, preferably, of a transparent plastic material, comprising between the halves 1 and 2 a filter 3 of porous material of plastic, nylon, teflon or some other organic or inorganic synthetic material. The pore size of these membranes is to be uniform and large (10 $\mu$m, for example), but smaller than the carrier particles or the materials used for absorbing the unbound ligands. The block half 1 has an inlet line 4 for the segmented stream, and another inlet line 5 for a diluent. These lines join together upstream of a separating chamber 6 which is formed by semicylindrical confronting recesses in the block halves 1 and 2 and divided by the membrane 3. At the opposite end of the chamber 6, downstream from the inlet lines, there is an outlet line 7 of adjustable cross section (not illustrated) in block half 1, and another outlet line 8 in block half 2. The volume of the liquid-air mixture that emerges from the outlet line 7 is adjusted and attuned to the magnitude of the vacuum that is applied to the outlet line 8.

During operation, the segmented fluid stream is thinned by the diluent before it reaches the chamber 6 and passes in segmented form below the membrane 3. The pressure created by the injection of the diluent and the constriction of the outflow through outlet line 7 forces excess liquid and particles smaller than the pore size of the filter to pass through the membrane. The filtration is also aided by a corresponding negative pressure applied to the outlet opening 8. The filtrates, which contain unbound tracers, that is, antigen in the example, can be used for the determination of the free radical by counting the radioactivity in the case of the radio-immune test, or in the case of the fluorescent immune test or enzyme immune test, by measuring the intensity of the fluorescence or of a variable of the enzyme reaction, such as the absorption for example. The tracer (antigen) bound to the solid phase remains, on account of its large particle size (which is usually greater than 20 $\mu$m), in the segmented stream, and is captured at the outlet 7. The material can then be delivered to a detection apparatus such as the one described further below for counting the radioactivity.

It is possible in this manner to count either the bound or the unbound tracers according to the outlet stream that is selected. In any case, the intensity of the negative pressure and the amount of diluent injected can be utilized to control the volume filtered through the membrane within very narrow and precise limits.

Many of the highly porous membranes easily assume a negative electrostatic charge and retain it, thereby affecting the operation of the membrane in many ways. For example, particles can be withheld which are smaller than the pore size. The electrostatic charge, however, can also be useful by holding to a minimum any clogging by larger particles present in the liquid and by particles brought into the system with the air.

The intensity of the electrostatic charge depends on the pH value, and can be modified by the use of diluent buffers having the desired pH. If the membrane is made of a conductive material, an outside source can be used to influence the charge. The diluent can also be a solution which performs a special function. It can contain a substance, for example, such as polyvinyl alcohol, which coats the membrane and thus, if desired, reduces the electrostatic charge. The diluent can also be a liquid which causes the precipitation of the carrier, such as for example a salt solution which produces a precipitating action on the carrier by increasing the ion concentration.

The counting of the radioactivity can be performed in an apparatus like the one represented in FIG. 2, which comprises a conventional gamma-ray counting head 21 which contains a closed cell 22. This cell is provided with an inlet tube 23 cooperating with an electrical sensor 24, and with an outlet tube 25 to which a vacuum is applied. The outlet tube 25 is connected by tube 26 and valve 27 to a hose pump or other aspirating means, the valve 27 being controlled by the sensor 24 and a time measuring apparatus which is not shown.

Alternatively, the tube 26 can be eliminated and the valve 27 directly connected to the outlet 25.

The sensor 24 responds to the properties of the wash liquids—to their color, for example—and when this characteristic property is detected, valve 27 is closed and the cell is filled, and then the counting begins. At the end of a predetermined length of time, the counter is stopped and reset to zero, while the valve 27 is opened and the cell is emptied by the vacuum that is constantly applied to the outlet 25. The count can be printed out or otherwise recorded or indicated. It is important that the counting method is based on a new concept, namely a "simultaneous feed count". Preliminary studies have shown that the relationship between the number of counting pulses and the time follows a curve which can be represented by a quadratic equation. This method of counting can be advantageous, since, when a minicomputer is used, great irregularity within a sample segment can result in plainly apparent deviations from a calculated curve. This can be detected and errors can be determined.

Referring now to FIG. 3, the further improved basic system will be described with the aid of an antigen determination by way of example. In this case, the reagents, which contain the antigen in the serum or urine, as described above, are fed through the coils 31, which are maintained at constant temperature, in a stream divided by air segments, to the separating apparatus 32 represented in FIG. 1, in which the dilution-forced filtration takes place. By the latter, the antigen bound to the solid phase is separated from the free and unbound antigen as well as the other serum components. The latter are discarded, while the segmented stream mixes with another specific antibody (which acts against the same antigen), but is tagged with $J^{125}$. The result is a second antibody reaction during the passage through an additional coil 33 maintained at constant temperature, which results in the formation of a marked complex in the solid phase, in that the antigen is present between two antibodies of which one is bound to the solid phase (immobilized antibody) and the other is tagged. After this reaction, the complex bound to the solid phase is separated from the tagged free antibody in a second separating device 34. The free fraction is then counted and the bound fraction is discarded, or vice versa.

The invention can also be used for the purpose of automating a conventional radio-immune test, i.e., a test in which the antibody is used as it is, without modification, bound, for example, to a solid phase. The automation of this test is achieved by mixing the segmented stream containing the incubated analysis material (e.g., the antibody, the tagged (tracer) and the untagged antigen) with a particulate material which is capable of binding itself either to the free component or to the bound component. An example of a material of the first kind is a porous ion exchange gel or ion exchange resin which is capable of capturing anionic or cationic particles, while an example of a material of the second kind is a second antibody which is covalently bound to a porous gel matrix, such as sephadex or sepharose.

The method of the invention is also suitable for automating the determination of steroids and medicaments or drugs, in which no extraction with an organic solvent is necessary. The method is also suited for the automation of test methods other than immune testing. For example, the determination of the entire iron binding capacity comprises the addition of excess iron salt for the purpose of saturating the carrier protein, transferrin. The separation of the excess iron can be performed in a flow system by mixing it with a porous cation exchanger and then performing the dilution-forced filtration. The iron in the filtrate can then be determined by conventional methods.

In summary, the method described is suitable for the automation of the radio-immune test, the enzyme immune test or the fluorescent immune test and other methods of determination in which particulate materials such as a porous gel or resin are used as analytic reagents. To achieve the best results, the particles should comprise an abrasion resistant matrix having a spherical shape and a uniform particle size.

EXAMPLE 1

Automated determination of thyroxin by using an arrangement according to FIG. 4, the enzyme reaction being omitted and the free fraction being measured on the counter according to the separating system. It can be conducted on the analytical automat "Auto-Analyzer" of the Technicon Company.

Turn on counter and interface:
1. Replace the membrane
2. Pump in the buffer so as to achieve a good bubble pattern through the filter. IMPORTANT!
3. Pump in the tracer to determine the total count rate (which is to amount to from 20 to 25,000).
4. Add the antibody and pump the dye through the specimen line.
5. When the dye hits, test the bond by activating the counter. Adjust the level.
6. Start taking the specimen.
Specimen plate = 5 × 'O'
   Standard curve
   2 control sera at 39 and 40
   8 specimens
   2 control sera etc.
7. Calculate in the conventional manner.

Reagents 1. (AB = insoluble antibody)
   Dilute 10 ml of sepharose T4 to 100 ml with tris buffer of a pH of 8.5
2. Tracer 1.0 ml (10 μl)
   40 ml of tris buffer
   4 ml of 5% albumin
   250 mg of A.N.S.
3. Wash solution: 1.8% NaCl + 1 ml Brij per liter
   Before use, filter through a 1 μm filter.
4. Dye: 15% beef albumin − 100 ml + 8 ml of green dye
5. Tris buffer: 12 g/l of tris buffer adjusted with
   HCl to a pH of 8.5. Add 2.5 g of azide and filter before use through a 1 μm filter.

Standard Solutions

Standard solution T4 'A': 57.21 mg of pure T4 in 6 ml of 0.1 n NaOH, add absolute ethanol to make 50 ml, and deep freeze.

Standard solution T4 'B': dilute 0.1 ml of the standard solution A with 1.9 ml of tris buffer containing 0.5% of albumin and deep freeze.

Working standard solution: 19.9 ml of 5% beef albumin plus 0.1 ml of standard solution B = 325 nmol/l. Double dilute with 5% human albumin (which has been treated with resin), with the formation of 163.82, 41.20 and 10 nmol/l.

6. Antibody: bind 1 ml of beneden T4 antibody to 5 kg of sepharose, dilute to 100 ml with tris buffer, add 0.1 g of azide, and deep freeze aliquot parts of 10 ml each.

Settings

Test time: 75 seconds; Wash time: 15 seconds;
Delay: 5 seconds; Count: 55 seconds;
Recording: 2 V.

EXAMPLE 2

Automated determination of thyroxin (T4) by the enzyme immune test according to FIG. 4, wherein a scheme of the implementation of the test is shown. Conducted on the analytic automat "Auto-Analyzer" of the Technicon Company.

The preparations are made as in the Radio-immune test of Example 1.

I. Reagents

1. T4 antibody
   Was bound covalently to BrCN-activated sepharose pursuant to instructions of the manufacturer (Pharmacia) and suspended in 0.1 M of tris-HCl buffer, pH = 8.5, with 0.1% of Brij, by means of a magnetic stirrer.
2. Tracer
   T4 was tagged with peroxidase (EC 1.11.1.7, Boehringer Mannheim, Cat. No. 15629) and diluted to a final volume of 50 ml with tris-HCl buffer, pH = 8.5, with 0.5% of albumin, 250 mg A.N.S. (8-anilinonaphthalinesulfonic acid-(1) ammonium salt) and 0.1% of Brij.
3. Diluent
   0.2 M of phosphate buffer, pH = 8.0, with 0.1% Brij.
4. Enzyme Reaction Mixture
   0.1 M phosphate buffer, pH = 8.0, with 11 mM of 2.4-dichlorophenol, 1.2 mM of 4-aminophenazone and 1.5 mM of sodium perborate.
5. Wash Solution:
   1.8% of NaCl with 0.1% Brij.

II. Performance

1. Rinse out with wash solution and establish a constant throughput of bubbles through the separator.
2. Feed in the tracer, add the enzyme reaction mixture, balance the photometer and set the recorder: determine the total activity of the tracer.

3. Add the T4 antibody, check the tracer binding, and again balance the photometer and recorder.
4. Begin taking the specimen
   Specimen plate:
   5 ml 'O' Standard ($=C_o$)
   Standard curve
   2 control serums
   8 specimens
   2 control serums
   8 specimens, etc.
5. Evaluate the results in the conventional manner on the basis of the recorder diagram.

If the enzyme tagging is replaced by fluorescent tagging and a fluorimeter is used, the FIA test can be performed in an analogous manner, e.g., with the use of a Perkin-Elmer spectral fluorimeter, Mod. 1000, or of a Kontron spectral fluorimeter model S FM 22.

We claim:

1. Method for the detection and for the determination of one component of the reaction between a specific binding protein and the corresponding bindable substance by the use of the binding affinity of these components for one another, in an automated system having a continuously flowing liquid stream, comprising introducing mixtures of sample material with (a) a determined amount of one component of the reaction in tagged form and (b) another, carrier-bound, component successively into said liquid stream by means of a fluid which is substantially non-miscible with said liquid stream so that the individual mixtures remain separate, incubating the mixtures, continuously introducing same into a separator and separating therein at least a portion of the liquid phase from the solid phase by filtration, and measuring the amount of the tagged component in one of the separated phases as a measure of the unknown component to be detected.

2. Method as claimed in claim 1 wherein the pressure in the continuously flowing liquid stream into the separator is increased before reaching the filtration zone, by the introduction of an additional liquid stream thereinto.

3. Method as claimed in claim 2 wherein additionally the pressure on the filtrate side of the filtration zone is lowered.

4. Method as claimed in claim 1 wherein the said fluid to separate the sample mixtures is constituted by gas bubbles segmenting the mixtures in the liquid stream.

5. Method as claimed in claim 1, wherein said fluid to separate said sample mixtures is a liquid substantially non-miscible with the continuously flowing liquid stream.

6. Method as claimed in claim 1, wherein the sample mixtures are introduced block-wise, without substantially altering the velocity of the continuously flowing liquid stream, into said stream.

7. Method as claimed in claim 1 wherein said tagged component is tagged radioactively or by an enzyme, or by a fluorescent radical.

8. Method as claimed in claim 1 wherein the specific binding protein is an antibody, anti-antibody, or a hormone receptor, and the corresponding bindable substance is antigen, haptene, or antibody, or a hormone, respectively.

9. Method as claimed in claim 1 wherein said carrier bound component is bound to an insoluble particulate carrier.

10. Method as claimed in claim 1 wherein said carrier bound component is bound to a carrier which is easily transformed to an insoluble particulate state just prior to the separation stage.

11. Method as claimed in claim 1 wherein said carrier bound component is bound to a carrier which is reversibly precipitatable and can be insolubilized prior to the separation stage and subsequently re-solubilized.

12. Method as claimed in claim 2 wherein said additional liquid stream is introduced just ahead of a filter membrane constituting the filtration zone.

* * * * *